United States Patent [19]

van Staaveren

[11] Plant 4,936

[45] Nov. 9, 1982

[54] CARNATION NAMED STAGOLD

[75] Inventor: Maurits C. van Staaveren, 30 Hornweg, at 1432 GM, Aalsmeer, Netherlands

[73] Assignees: B. V. Handelskwekerij; M. C. van Staaveren, both of Aalsmeer, Netherlands

[21] Appl. No.: 225,331

[22] Filed: Jan. 15, 1981

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—C. W. Rummler

[57] ABSTRACT

A new variety of carnation of the spray or miniature type distinguished by its medium sized, bright yellow flowers each borne singly on a strong, erect and relatively long pedicel; its continuous and profuse blooming habit; and its moderately abundant blue-green foliage.

1 Drawing Figure

BACKGROUND OF THE NEW PLANT

This carnation variety originated as a sport of the variety "Ministar" (unpatented) and was discovered by me in 1975 among nursery plants grown at Aalsmeer, The Netherlands, for breeding purposes. The bright yellow coloration of the inflorescence and the profuse display of blooms led me to reproduce this plant by cuttings for test and observation and further propagation through successive generations at Aalsmeer, The Netherlands, has shown that its novel characteristics hold true from generation to generation and appear to be firmly fixed. Propagation of this plant for commercial purposes is presently being carried on, by means of cuttings, at the Aalsmeer nurseries.

DESCRIPTION OF THE DRAWING

This new variety of carnation plant is illustrated by the accompanying full color photographic drawing, which shows a full stem bearing a spray comprising buds and fully opened flowers which demonstrate the flowering habit of the new plant and its floral coloration, the colors shown being as nearly true as it is reasonably possible to obtain by conventional photographic procedures.

DESCRIPTION OF THE NEW PLANT

The following is a detailed description of my new variety of carnation plant based upon observations of plants grown under conventional greenhouse practices, the color designations being according to The R.H.S. Colour Chart published by The Royal Horticultural Society of London, England.

THE PLANT

Origin: Sport.
Parentage: Ministar (unpatented).
Classification:
- *Botanic.*—*Dianthus caryophyllus.*
- *Commercial.*—Spray or miniature carnation.

Form: Bush.
Height: About 1 to 1.2 m.
Growth: Vigorous and upright with moderate strength.
Branching: Normal.
Foliage:
- *Quantity.*—Moderate.
- *Leaf size.*—Moderate.

- *Leaf shape.*—Oblong.
- *Texture.*—Smooth.
- *Color.*—Upper side — Blue-Green. Under side — Blue-Green.

THE BUD

Size: Medium, about 15 mm. in diameter and about 40 mm. long.
Form: Generally ovoid with cuspidate apex.
Opening rate: Moderate.
Color:
- *When sepals first divide.*—Yellow-Green.
- *When petals begin to unfurl.*—Yellow-Green.

Sepals:
- *Condition.*—Upstanding.
- *Color.*—Inside — Grey-Green. Outside — Yellow-Green with White tips.

Calyx:
- *Shape.*—Tubular.
- *Size.*—Moderate, about 15 mm. broad and about 15 mm. long.
- *Splitting.*—The calyx does not split.
- *Aspect.*—Smooth.

Peduncle: Rigid and erect.
- *Color.*—Grey-Green.

THE FLOWER

Blooming habit: Continuous and profuse.
Size of bloom: Medium.
- *Diameter.*—About 55 mm.
- *Depth.*—About 30 mm.

Borne: Singly.
Shape: High center when bloom opens. The form does not change.
Petalage:
- *Number of petals.*—About 35.
- *Arrangement.*—Generally imbricated.
- *Color.*—Outer and inside petals — RHS 10C. Reverse side — RHS 10C.
- *Texture.*—Soft.
- *Appearance.*—Shiny.

Peduncle: Sturdy and upright.
- *Length.*—About 45 cm.
- *Color.*—Grey-Green.

Persistence: The flowers hang on and dry.
Fragrance: None.
Lasting quality:

*On plant.*—About 14 days.
*As a cut flower.*—About 10 days.

REPRODUCTIVE ORGANS

Stamens: Anthers and pollen are rarely present.
Pistils: About 3 in number.
*Length.*—About 40 mm.
*Stigmas.*—Color — Cream Yellow.
Fruit: Fertile.

*Shape.*—Cylindrical/round.
*Color.*—Green/Brown at maturity.

I claim:

1. A new and distinct variety of carnation plant, substantially as herein shown and described, characterized by its high productivity of bright yellow flowers borne singly on rigid, erect pedicels carried in spray arrangement on a sturdy, upright peduncle.

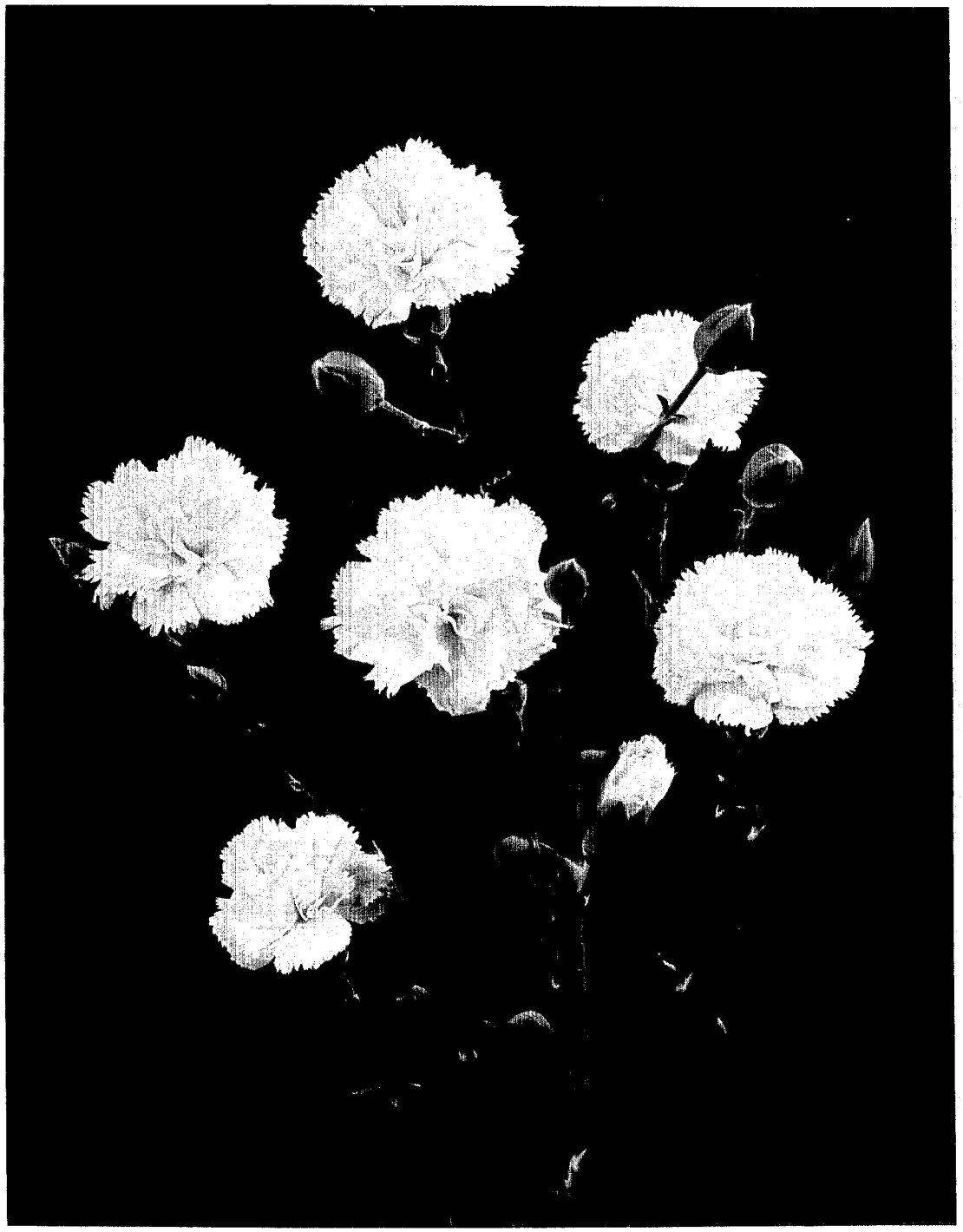

* * * * *